United States Patent
Wernik et al.

(10) Patent No.: US 9,310,451 B2
(45) Date of Patent: Apr. 12, 2016

(54) MAGNETIC RESONANCE-BASED METHOD AND SYSTEM FOR DETERMINATION OF OXYGEN SATURATION IN FLOWING BLOOD

(75) Inventors: Christopher Wernik, Toronto (CA); Venkat Swaminathan, Toronto (CA); Graham Wright, Toronto (CA); Christopher MacGowan, Toronto (CA)

(73) Assignees: The Hospital for Sick Children, Toronto, Ontario (CA); Sunnybrook Health Sciences Centre, Toronto, Ontario (CA)

( * ) Notice: Subject to any disclaimer, the term of this patent is extended or adjusted under 35 U.S.C. 154(b) by 700 days.

(21) Appl. No.: 13/576,676

(22) PCT Filed: Apr. 15, 2011

(86) PCT No.: PCT/CA2011/000429
§ 371 (c)(1),
(2), (4) Date: Aug. 2, 2012

(87) PCT Pub. No.: WO2011/127590
PCT Pub. Date: Oct. 20, 2011

(65) Prior Publication Data
US 2013/0088227 A1 Apr. 11, 2013

Related U.S. Application Data

(60) Provisional application No. 61/324,807, filed on Apr. 16, 2010.

(51) Int. Cl.
*G01R 33/483* (2006.01)
*A61B 5/026* (2006.01)
*A61B 5/145* (2006.01)
(Continued)

(52) U.S. Cl.
CPC ............ *G01R 33/483* (2013.01); *A61B 5/0263* (2013.01); *A61B 5/14542* (2013.01); *A61B 5/7257* (2013.01); *G01R 33/28* (2013.01); *G01R 33/50* (2013.01); *G01R 33/56509* (2013.01);
(Continued)

(58) Field of Classification Search
CPC .................................................... G01R 33/483
See application file for complete search history.

(56) References Cited

U.S. PATENT DOCUMENTS 5,233,298 A 8/1993 Dumoulin
5,233,991 A 8/1993 Wright
(Continued)

OTHER PUBLICATIONS

Canadian Intellectual Property Office, "International Search Report" for corresponding International Patent Application No. PCT/CA2011/000429, dated Jun. 1, 2011, Canada.
Nield, L. et al., "In Vivo MRI Measurement of Blood Oxygen Saturation in Children with Congenital Heart Disease", Pediatric Radiology, vol. 35, No. 2, pp. 179-185, Oct. 2004.

*Primary Examiner* — Dixomara Vargas
(74) *Attorney, Agent, or Firm* — Norton Rose Fulbright Canada LLP

(57) ABSTRACT

A method and system for determination of oxygen saturation in blood flowing in a vessel using magnetic resonance (MR). An MR image sequence is acquired with different echo time (TE) encoding, and different Fourier velocity encoding (FVE). A Fourier transformation is applied along the velocity dimension to determine a velocity distribution of tissue signals in each voxel of the image sequence. Tissue signals indicative of moving tissues are separated from tissue signals indicative of static tissue, based on the velocity distribution. Oxygen saturation in blood may then be determined using only the tissue signals indicative of flowing blood.

24 Claims, 11 Drawing Sheets

(51) Int. Cl.
*A61B 5/00* (2006.01)
*G01R 33/50* (2006.01)
*G01R 33/565* (2006.01)
*G01R 33/28* (2006.01)
*A61B 5/02* (2006.01)
*A61B 5/11* (2006.01)
*G01R 33/563* (2006.01)

(52) U.S. Cl.
CPC ........... *A61B 5/02007* (2013.01); *A61B 5/1128* (2013.01); *G01R 33/56316* (2013.01)

(56) References Cited

U.S. PATENT DOCUMENTS 8,041,459 B2 * 10/2011 Sutherland ............. A61B 19/22
600/407
2003/0214288 A1  11/2003 MacGowan et al.
2013/0144140 A1 * 6/2013 Frederick ............. A61B 5/0042
600/324

* cited by examiner

MAGNETIC RESONANCE-BASED METHOD AND SYSTEM FOR DETERMINATION OF OXYGEN SATURATION IN FLOWING BLOOD

CROSS-REFERENCE TO RELATED APPLICATION

The present disclosure claims priority from U.S. provisional patent application No. 61/324,807, filed Apr. 16, 2010, the entirety of which is hereby incorporated by reference.

TECHNICAL FIELD

The present disclosure relates generally to magnetic resonance techniques for differentiation of tissue signals. In particular, the present disclosure may be useful for determination of oxygen saturation in blood flowing in a vessel.

BACKGROUND

In magnetic resonance imaging (MRI), signals obtained from moving tissues (e.g., flowing blood) may be contaminated with signals from static tissues (e.g., vessel wall), in an example of partial volume effects. This may be particularly challenging where spatial resolution is low. MRI has been used for oximetry, but partial volume effects may affect the accuracy of the measurement.

The use of oximetry is a well understood and recognized technique for the measurement of blood oxygen saturation levels. However, conventional non-invasive oximetry methods may not be suitable in some cases, for example in premature babies with patent ductus arteriosus (PDA). PDA is a heart problem that occurs soon after birth in some babies. In PDA, abnormal blood flow occurs between two of the major arteries connected to the heart as a consequence of the blood vessel (called the ductus arteriosus), normally a component of fetal blood circulation, not closing shortly (typically hours to days) after the baby's birth. In such cases, there is typically a need to use cardiac catheterization, a more invasive form of intermittent blood sample, to determine arterial blood gases. The invasive nature of this pulmonary artery oxygen measurement may be stressful for the patient, for example an already fragile infant. Non-invasive techniques may be erroneous or may provide only indirect and/or very rough estimates of blood oxygen levels in such patients (e.g., limited to peripheral vessels).

MRI, a technique for non-invasive imaging of adults and children, has been used for non-invasive measurement of oxygen saturation of blood. For example, U.S. Pat. No. 5,233, 991, the entirety of which is hereby incorporated by reference, describes a method and apparatus for estimating blood oxygen saturation using magnetic resonance (MR). This MR oximetry may be based on a quantification of T2 relaxation time. However, this conventional MR oximetry technique may be unsuitable for accurate determination of oxygen saturation in relatively small blood vessels (e.g., vessels in infants and children). As such, this technique has seen relatively little application to use in neonatal infant care.

There is an inherent MR tradeoff between spatial resolution and signal-to-noise ratio. With insufficient spatial resolution (e.g., as in relatively small blood vessels), T2 measurements may become biased by partial volume effects (e.g., where the image pixel or voxel is so large relative to the vessel cross-section that the vessel occupies only part of the pixel or voxel). This may be overcome by increasing the spatial resolution (e.g., using smaller image pixels or voxels), but this typically leads to a decrease in signal-to-noise of the measurement and, as a result, may produce less accurate T2 values. Increasing the spatial resolution may also require a longer time for image acquisition, which may be unsuitable for very young patients or any other patients who are unable to hold still for a lengthy period of time.

SUMMARY

In the present disclosure, an MR-based method and system is described. The method and system includes the use of a technique along a velocity dimension of a three-dimensional MR data set. A velocity distribution within an imaged voxel is determined, in which signals from moving tissue (e.g., blood within the vessel) and surrounding static tissue (e.g., the vessel wall) are separated, which may help to overcome partial volume effects without having to increase the spatial resolution. This may be useful for determining blood oxygen saturation.

In some aspects there is provided a method for determination of oxygen saturation in blood flowing in a vessel using magnetic resonance (MR), the method comprising: obtaining signals representing an MR image sequence of the vessel, the image sequence including a plurality of image data sets with different echo time (TE) encoding, and different Fourier velocity encoding (FVE), the FVE being obtained using different bipolar gradients having different areas (e.g., different amplitudes and/or time scalings) to encode respective different velocities for each TE, the FVE defining a velocity dimension in the MR image sequence; for each TE, applying a Fourier transformation along the velocity dimension to determine a velocity distribution of tissue signals in each voxel of the image sequence; determining tissue signals indicative of flowing blood apart from tissue signals indicative of static tissue, based on the velocity distribution; and determining oxygen saturation in blood using only the tissue signals indicative of flowing blood.

In some aspects, there is provided a system for determination of oxygen saturation in blood flowing in a vessel using MR, the system comprising a processor for executing instructions to cause the system to: receive signals representing an MR image sequence of the vessel, the image sequence including a plurality of image data sets with different TE encoding, and different FVE, the FVE being obtained using different bipolar gradients having different areas (e.g., different amplitudes and/or time scalings) to encode respective different velocities for each TE, the FVE defining a velocity dimension in the MR image sequence; for each TE, apply a Fourier transformation along the velocity dimension to determine a velocity distribution of tissue signals in each voxel of the image sequence; determine tissue signals indicative of flowing blood apart from tissue signals indicative of static tissue, based on the velocity distribution; and determine oxygen saturation in blood using only the tissue signals indicative of flowing blood.

In some aspects, there is provided a computer program product for determination of oxygen saturation in blood flowing in a vessel using MR, the computer program product having encoded thereon computer executable instructions for: obtaining signals representing an MR image sequence of the vessel, the image sequence including a plurality of image data sets with different TE encoding, and different FVE, the FVE being obtained using different bipolar gradients having different areas (e.g., different amplitudes and/or time scalings) to encode respective different velocities for each TE, the FVE defining a velocity dimension in the MR image sequence; for each TE, applying a Fourier transformation along the velocity dimension to determine a velocity distribution of tissue signals in each voxel of the image sequence; determining tissue signals indicative of flowing blood apart from tissue signals indicative of static tissue, based on the velocity distribution; and determining oxygen saturation in blood using only the tissue signals indicative of flowing blood.

BRIEF DESCRIPTION OF THE DRAWINGS

Reference will now be made to the drawings, which show by way of example embodiments of the present disclosure, and in which.

DETAILED DESCRIPTION

MR may be used for measuring or estimating blood oxygen saturation (% $O_2$), for example as described in U.S. Pat. No. 5,233,991, the entirety of which has been incorporated by reference above. This measurement may also be referred to as MR oximetry.

MR oximetry is based on the quantification of T2 relaxation time, a tissue-specific MR parameter that describes MR signal decay, and for blood, is directly related to oxygenated hemoglobin saturation (% $HbO_2$) or % $O_2$ by the following expression:

$$\frac{1}{T2} = \frac{1}{T2o} + K\left(1 - \frac{\% O_2}{100}\right)$$

where T2o is the T2 of fully oxygenated blood (i.e., % $O_2$=100) and K is a constant that depends on fibrinogen levels. By acquiring a set of T2-weighted MR images across a vessel, it is possible to measure the T2 of blood within it and hence the blood oxygen saturation level may be determined.

To acquire an MR image sequence data set for this calculation, an MRI pulse sequence, for example as described in the following steps, may be applied:

1) Tissue signals are weighted according to their respective T2 relaxation times using multiple 180° refocusing radio frequency (RF) pulses that are equally spaced in time.
2) At echo time, a slice-selective RF pulse is applied to initiate the data acquisition process. The RF pulse may be designed to suppress signal from fat and retain signal from tissue water.
3) The tissue signals are measured, for example using a spiral k-space trajectory.
4) The pulse sequence is repeated for multiple TEs. The image data obtained from application of each pulse sequence may be referred to as an echo.

The resultant MR data set comprises voxels containing tissue signals for a defined region of tissue. To estimate the T2 of blood, a region of interest (ROI) may be selected (e.g., by a clinician) within the vessel and the signal intensities of the voxels within the ROI may be averaged for each echo. The averaged data may be fit to the following monoexponential decay function, resulting in a T2 estimate:

$$S = A * \exp^{-TE/T2}$$

Figure 3:
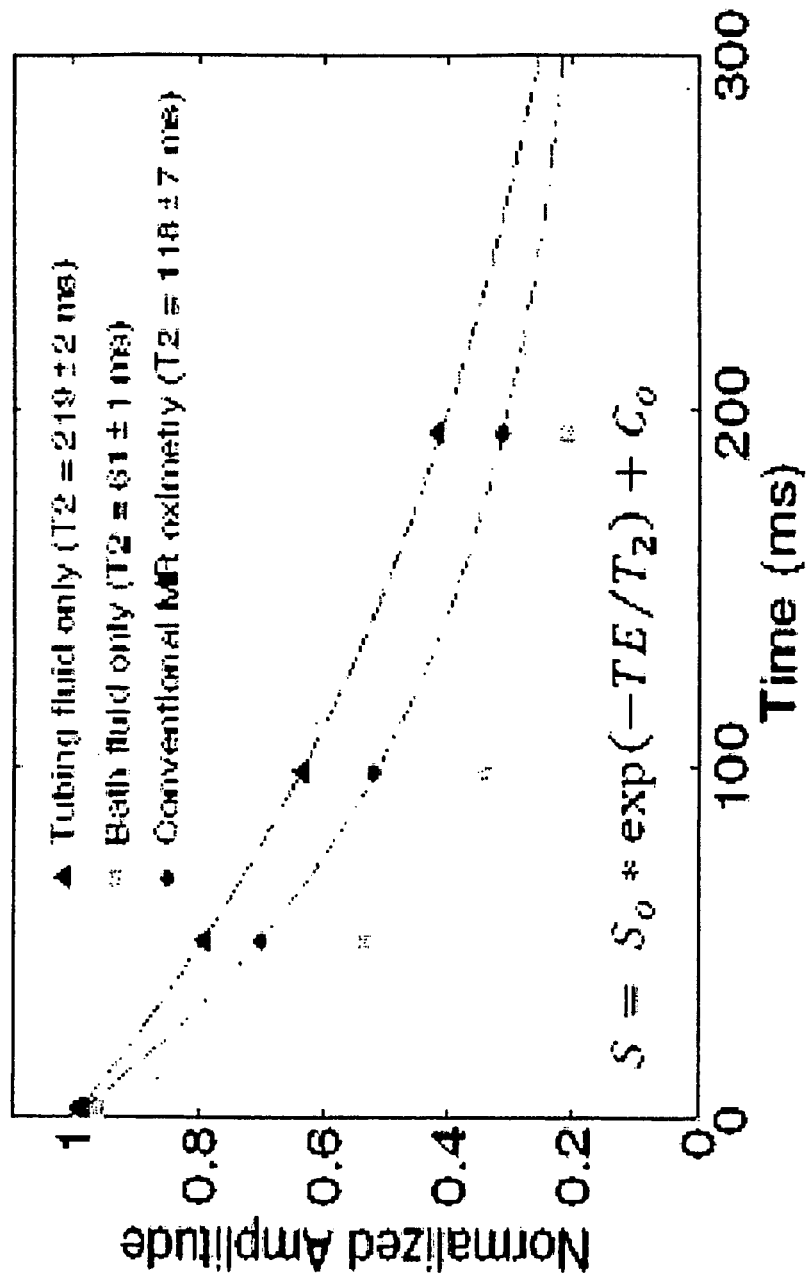
FIG. 3 is a plot showing example T2 decay curves of phantom components, compared to an example conventional method.

In some examples (e.g., as shown in the equation of FIG. 3), a constant may be included in the above fit. This constant may vary depending on, for example, whether the imaging was performed in vivo or in vitro, the type of doping agent used, etc.

Problems may arise when studying narrow vessels, such as those in infants and the coronary arteries of adults, for example due to the inherent MR tradeoff between spatial resolution and signal-to-noise ratio (SNR). With insufficient spatial resolution, T2 measurements may become biased by partial-volume effects, in which a single voxel contains signals corresponding to different tissue types (e.g., blood in a vessel and the vessel wall). This can be overcome by increasing the spatial resolution but doing so may decrease the SNR of the measurement and may produce less accurate T2 values.

The presently disclosed method and system may be useful in addressing one or more of these limitations by incorporating FVE into the pulse sequence. FVE encodes velocity using a bipolar gradient aligned with the direction of flow (e.g., perpendicular to the imaging plane). In some examples, the direction of flow may be oblique to the imaging plane, in which case the FVE may encode only for the flow component that is perpendicular to the imaging plane, which may result in an apparently lower measured velocity. This may be taken into account when making calculations using determined velocity distributions (e.g., through the use of a scaling factor). In some examples, FVE may be carried out in multiple dimensions, which may require a longer scan time (e.g., three-dimensional FVE may result in a doubled or tripled scanning time). Where it is known that flow is largely in a direction other than the usual gradient axis, the bipolar gradient may be oriented along another of the coordinate axes (e.g., Gx or Gy instead of Gz, in FIG. 1) in order to capture as much of the flow component as possible. Alternatively, where flow is known to be largely in a direction other than the usual gradient axis, the imaged slice may be oriented perpendicular to the direction of flow, without changing orientation of the gradient.

In an example pulse sequence incorporating FVE, the bipolar gradient may be applied immediately or very shortly after the spectral-spatial RF pulse and induces a velocity-dependent phase shift in proton spins. For each echo, several velocity encoding steps may be used by acquiring multiple two-dimensional images with different bipolar gradient areas (e.g., different amplitudes and/or time scalings) and a three-dimensional data set may be thus acquired, with velocitysensitivity as the third dimension. The application of a Fourier transformation along the third (i.e., velocity-encoding) dimension produces a velocity distribution in which the signals from moving blood and surrounding static tissue are associated with different velocities (i.e., non-zero velocity for flowing blood and zero or near-zero velocity for surround tissue) and thus may be separated based on their velocities, which may help to overcome partial volume effects.

Figure 5:
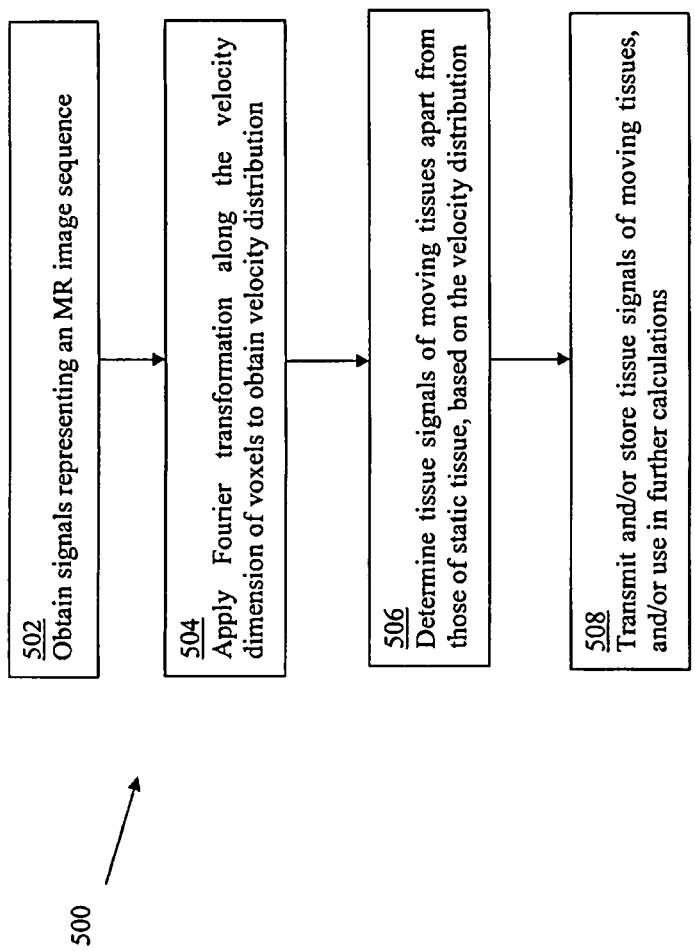
FIG. 5 is a flowchart illustrating an example of the disclosed method.

FIG. 5 is a flowchart illustrating an example method 500 for velocity-based differentiation of tissue signals in MRI, for example including determination of T2 values for moving tissues and determination of oxygen saturation in flowing blood. The example method 500 may be referred to as MR oximetry with velocity encoding (MOVE).

At 502, signals representing an MR image sequence may be obtained. The image sequence may include a plurality of image data sets with different TE encoding, and different bipolar gradients that provide FVE. The image sequence may be acquired, for example, using the example pulse sequence shown in FIG. 1. Other pulse sequences may be used, such as any appropriate variation to the example sequence of FIG. 1.

Figure 1:
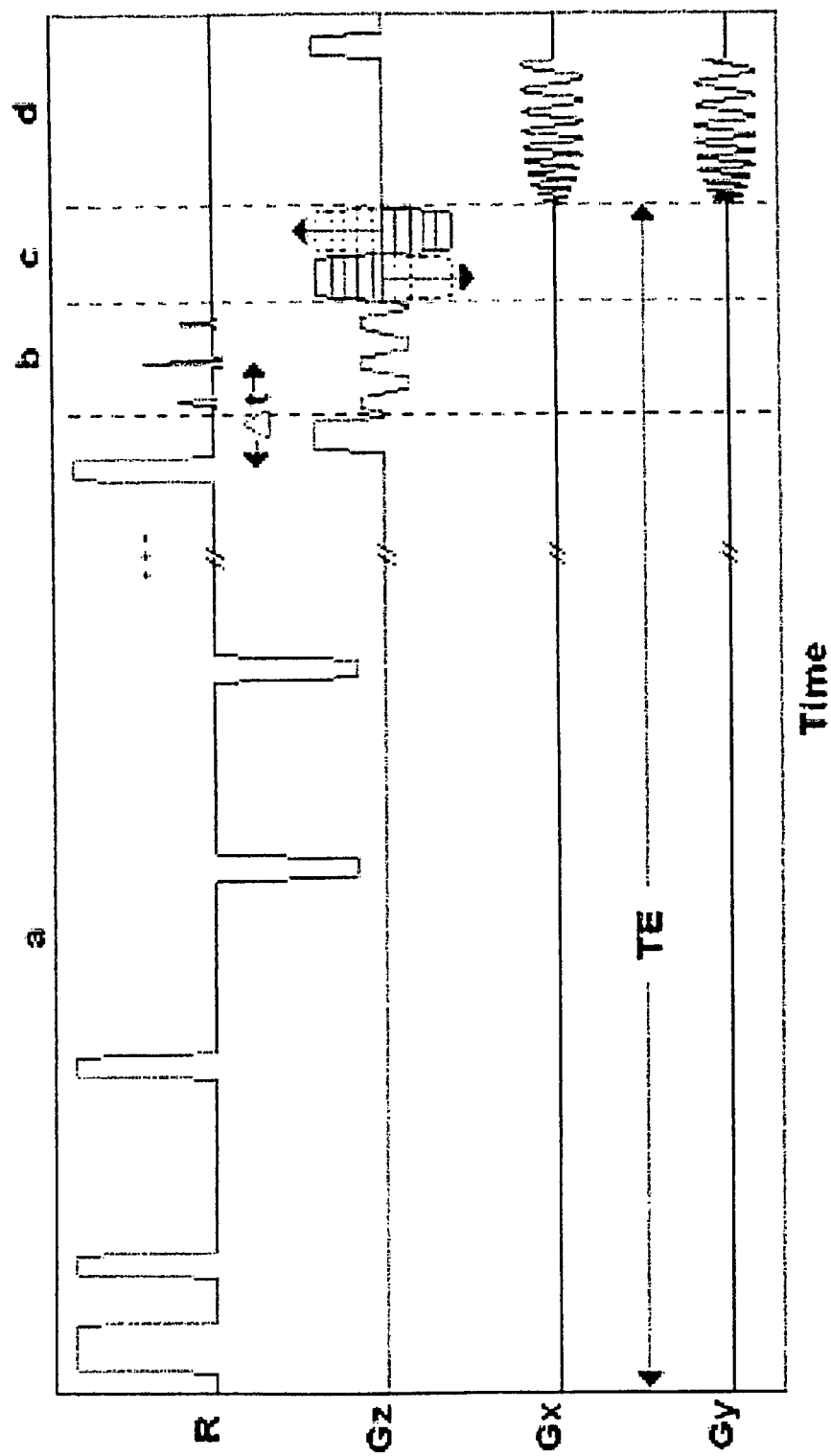
FIG. 1 shows an example pulse sequence diagram suitable for an example of the disclosed method and system.

The example pulse sequence of FIG. 1 may be based on the example pulse sequence steps described above. The example pulse sequence may include: (a) a nonselective, flow-insensitive T2 preparation of longitudinal magnetization (e.g., as described in step 1) above); (b) a spectral-spatial RF excitation (e.g., as described in step 2) above); (c) a bipolar flow encoding gradient; and (d) an interleaved spiral acquisition (e.g., as described in step 3) above). This pulse sequence may be repeated for different values of TE. In some examples, the pulse sequence may be concluded with a B1-independent rotation (BIR4) excitation to reset longitudinal magnetization (not shown). Upon scanning, a 4D MR image sequence dataset S(TE,kx,ky,kv) (with each voxel at (x,y) being encoded for velocity (v) at each TE) may be acquired, where kv is the velocity frequency variable encoded by the bipolar gradient (e.g., in (c)). The image sequence may include a plurality of image data sets each corresponding to a different TE, and each image data set may include a plurality of image data having different velocity encoding.

In some examples, where the flow is pulsatile (e.g., in an artery), the image acquisition may be gated (e.g., to the cardiac cycle), such that the flow may be substantially the same for each data acquisition. Where the flow is relatively stable, such gating may not be required. In some examples, even for pulsatile or otherwise uneven flow, no gating may be performed, with the result that over time, the mean velocity profile over a time period (e.g., a cardiac cycle) may be captured, independent of TE.

At 504, a Fourier transformation may be applied to the image data set (kx,ky,kv) to determine the velocity distribution of tissue signals in each voxel of the image sequence. For example, a 2D inverse fast Fourier transform (IFFT) may be applied to the data set along kx and ky, and then a further IFFT may be applied along the velocity dimension (kv) at each voxel (x,y). Alternatively, a 3D IFFT, may be performed along kx, ky and kv at each TE, resulting in S(TE,x,y,v).

An ROI may be selected, which may include one or more voxels corresponding to blood within a vessel. Such selection may be done manually, for example by a clinician. Signals from selected voxel(s) may be used to determine oxygen saturation levels. The voxel(s) may be selected to target those voxel(s) having at least a portion that may correspond to blood in a vessel. Such voxel(s) may include those that cover only flowing blood (i.e., is located entirely within the walls of the vessel) as well as those that cover both flowing blood and the vessel wall. Signals from voxel(s) covering both flowing blood and the vessel wall may suffer from partial volume effects unless signals arising from non-blood tissues are separated out.

In some examples, the ROI may be selected prior to applying the Fourier transformation and the Fourier transformation may be only applied to voxel(s) belonging to the selected ROI, which may be useful in reducing the amount of processing time and/or power required. In other examples, the Fourier transformation may be applied to all voxels of an image, and data corresponding to a selected ROI may be extracted afterwards.

At 506, tissue signals indicative of moving tissues (e.g., flowing blood) may be determined apart from tissue signals indicative of static tissue, based on the velocity distribution. For example, flowing blood may be represented by a flow-dependent velocity distribution covering a range of non-zero velocities, and surrounding tissue may be represented by a peak at zero or non-zero velocity. Thus, it may be possible to determine signals indicative of flowing blood apart from signals indicative of static tissue based on the velocity distribution. For voxel(s) (x,y) covering a vessel, a plot along the v-axis generates a T2-weighted velocity distribution in which signals from moving blood (i.e., signals corresponding to non-zero velocity) may be separated from that of surrounding static tissue (i.e., signals corresponding to zero or near-zero velocity).

The resolution of the velocity distribution may also be controlled by the FVE step in the pulse sequence. For example, velocity encoding may encode velocities at 0, 10, 20, 30 and 40 cm/s. Thus, tissues that exhibit slow movement having non-zero velocity but less than 10 cm/s velocity (e.g., pulsing vessel wall or surrounding tissues) may be encoded as having 0 cm/s velocity and thus may be considered "static".

Velocity encoding may be made finer, for example, by using a greater number of different bipolar gradients and/or a greater bipolar area. Finer velocity encoding may require longer scanning time to allow for a greater number of different bipolar gradients. Such finer velocity resolution may be useful, for example, for obtaining relatively detailed velocity information and for certain velocity calculations (e.g., for calculation of velocity distributions over time).

Where the velocity resolution is finer, minor velocity fluctuations (e.g., in slow pulsing vessel walls) may be filtered out by the use of velocity ranges or "bins". For example, the velocity distribution may be partitioned into "bins" or defined ranges, such as 0-9.9 cm/s, 10-19.9 cm/s, 20-29.9 cm/s, 30-39.9 cm/s, and 40 cm/s and above, which may be of equal or unequal sizes. The use of such bins may be useful in filtering out minor velocity fluctuations. For example, vessel walls and surrounding tissue may exhibit small movement (e.g., slow pulsations much slower than blood flow) that may fall into the 0-9.9 cm/s bin, thus signals from tissues exhibiting such small movements may be associated with static tissue.

In some examples, minor and/or slow movements (e.g., pulsing), such as in vessel wall and surrounding tissues, may also be largely parallel to the imaging plane (i.e., perpendicular to the direction of velocity encoding) and thus may not appear in the velocity distribution.

At 508, signals representative of tissue signals indicative of moving tissues may be transmitted, stored and/or used in further calculations (e.g., determination of T2 decay values, further oxygen saturation calculations, or other T2 calculations). For example, oxygen saturation in flowing blood may be determined without contamination from vessel signals by using only the non-zero velocity portion of the signals in the calculation. This may be done by, for example, determining T2 decay by using only the signals from each TE that have non-zero velocity and this T2 value may be used for determining oxygen saturation.

An example calculation for T2 is now described, using signal amplitudes plotted along the velocity distribution. Signals corresponding to zero or near-zero velocities of the velocity distribution may be discarded. The T2 decay value may be calculated separately based on signal amplitudes for each velocity bin. A weighted average of the calculated T2 values may be performed, for example based on the signal amplitudes (e.g., signal-to-noise ratios) of the corresponding bin. This weight average may be then used as the T2 value of the flowing tissue. In another example, after calculating the T2 value for each bin, the values corresponding to non-zero velocities may be used in a simple average to determine the T2 value of the flowing tissue.

The number of velocity encoding steps, combined with the velocity encoding (VENC) parameter, may determine the velocity field of view (FOV) and resolution of the velocity distribution. By analyzing the T2 decay from flowing blood only (i.e., corresponding to non-zero velocity signals), it may be possible to quantify T2 more accurately in smaller vessels.

The T2 value determined from non-zero velocity signals (e.g., indicative of flowing blood) alone may be used to determine the oxygen saturation level in the blood, without contamination from partial volume effects. This may be useful for smaller vessels where there may be relatively few or no voxels that do not include the vessel wall.

An example system suitable for carrying out the above method is now described. The system may include a processor (e.g., an imaging workstation) for executing instructions to carry out the method described above. The system may further include a memory for storing received and calculated data. The system may further include a display for providing calculated data to a user. The system may further include an input system (e.g., a keyboard and/or a mouse) for receiving input from a user. The system may communicate with an MR image acquisition system to receiving the MR image sequence data, or the system may include the MR image acquisition system.

Although a method is described, it should also be understood that the disclosure also includes an article of manufacture, such as a pre-recorded storage device or other similar computer readable medium having program instructions tangibly recorded thereon, or a computer data signal carrying computer readable program instructions or code, that may direct a processor to carry out the disclosed method.

Although blood oxygen saturation has been described, the disclosed method and system may also provide velocity data, which may be useful for other calculations, not available using conventional oximetry techniques. For example, the velocity data may be useful, when used with calculated oxygen saturation data, for determining total oxygen transport in a vessel. In general, the disclosed method and system may allow for reduction or elimination of partial volume effects, and may allow for imaging using coarser spatial resolution.

EXAMPLES

Examples of the disclosed method and system are now described. These examples are provided for the purpose of illustration only and are not intended to be limiting.

In one example, an example of the disclosed method and system is used to calculate T2 and oxygen saturation in a phantom. The disclosed method is compared with a conventional method.

In the phantom, to mimic blood flowing in a vessel, water was pumped through a thin-walled (e.g., thickness=0.5 mm) latex tube at a constant flow rate by a computer-controlled gear pump. The tube was immersed in a water bath to mimic static tissue surrounding the vessel and a contrast agent, in this example gadopentetate dimeglumine (e.g., Magnevist™, Berlex, Canada) was used to adjust the tubing and bath T2 values to represent arterial blood and tissue, respectively. Imaging was performed on a 1.5 T MR system (GE Healthcare, USA) using the body coil.

Figure 2:
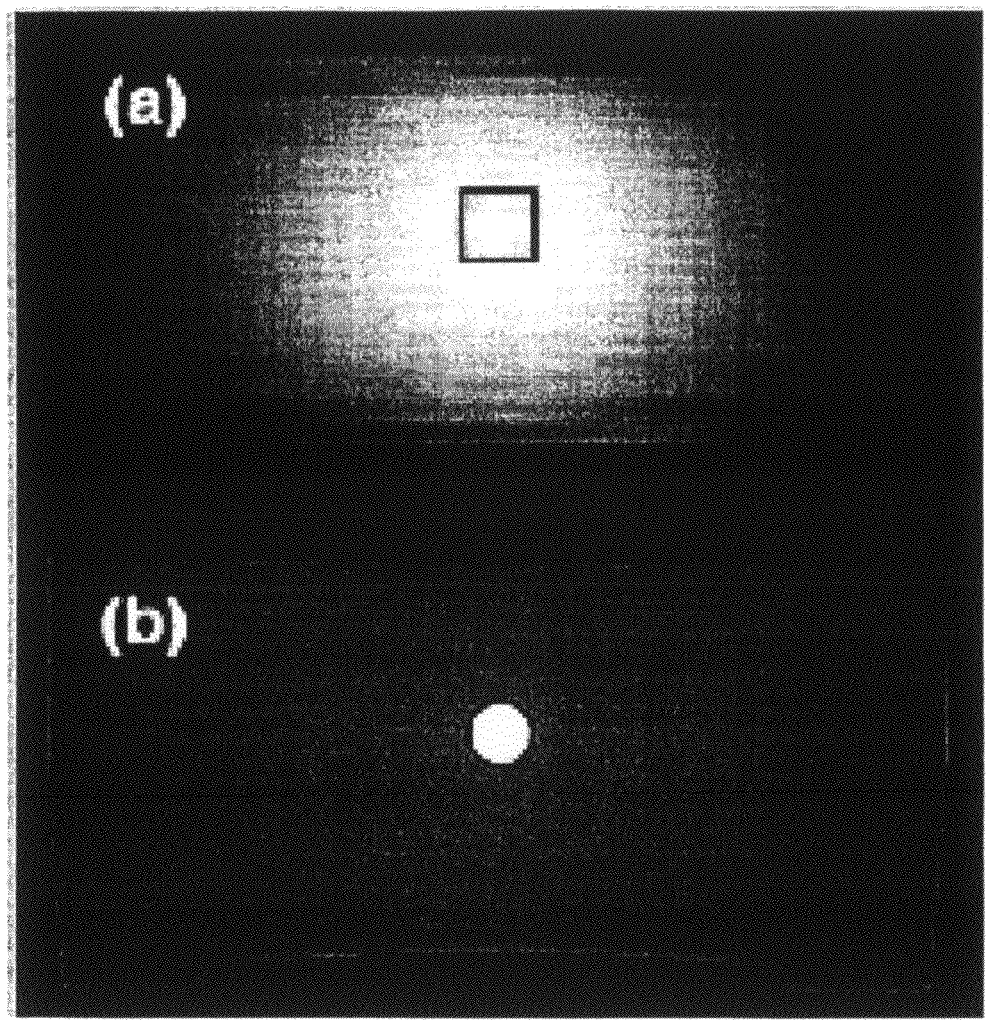
FIG. 2 shows examples of image slices acquired in a phantom at low and high spatial resolutions.

To consider the suitability of the disclosed method in the presence of partial volume effects, two low spatial resolution datasets were acquired:

S1(TE,kx,ky) using conventional MR oximetry with TE=[2.9, 50.7, 98.5, 194] ms, TR=1.5 s, $\Delta x = \Delta y = 5$ mm, scan time≈18 s, and S2(TE,kx,ky,kv) using an example of the disclosed method with TE=[7.6, 55.4, 103.2, 198.7] ms, TR=1.5 s, $\Delta x = \Delta y = 5$ mm, VENC=40 cm/s, velocity resolution=10 cm/s, scan time≈2 m 24 s. The difference in TE may be a result of the including of a bipolar gradient in the example of the disclosed method. The imaged slice corresponding to S1(2.9 ms,x,y) is shown in FIG. 2a, at low spatial resolution, along with a high spatial resolution reference (not used in calculations) in FIG. 2b. Although in this example the scan time was about 2 m 24 s, this relatively long scan time was used for the purpose of this example. In other uses, scan times may be shorter (e.g., just about or less than one minute). For example, in some in vivo scans, the scan time may be about 12 s or shorter, which may be repeated (e.g., for about 1 m total).

At the imaged spatial resolution, partial volume effects were found to contaminate all vessel voxels. An ROI encompassing the vessel (box in FIG. 2a) was selected and the signal intensities averaged to produce S1,ROI(TE) and S2,ROI(TE,v). A least-squares fit was then applied to the averaged data according to the equation in FIG. 3, where $C_o$ accounts for T1 relaxation during the time interval $\Delta t$ shown in FIG. 1.

In the case of S2,ROI, the fit was performed at each velocity and the result for tubing T2 taken as the weighted mean of each non-zero velocity T2 estimate.

Reference T2 relaxation curves measured in isolated samples of the tubing and bath fluids are shown in FIG. 3 (T2=219±2 ms and 61±1 ms, T1≈250 and 80 ms, respectively). Also shown is the conventional MR oximetry measurement of tubing fluid with a T2 estimate of 118±7 ms, indicating significant partial volume errors compared to the T2 of the tubing fluid (i.e., flowing fluid) alone.

Figure 4:
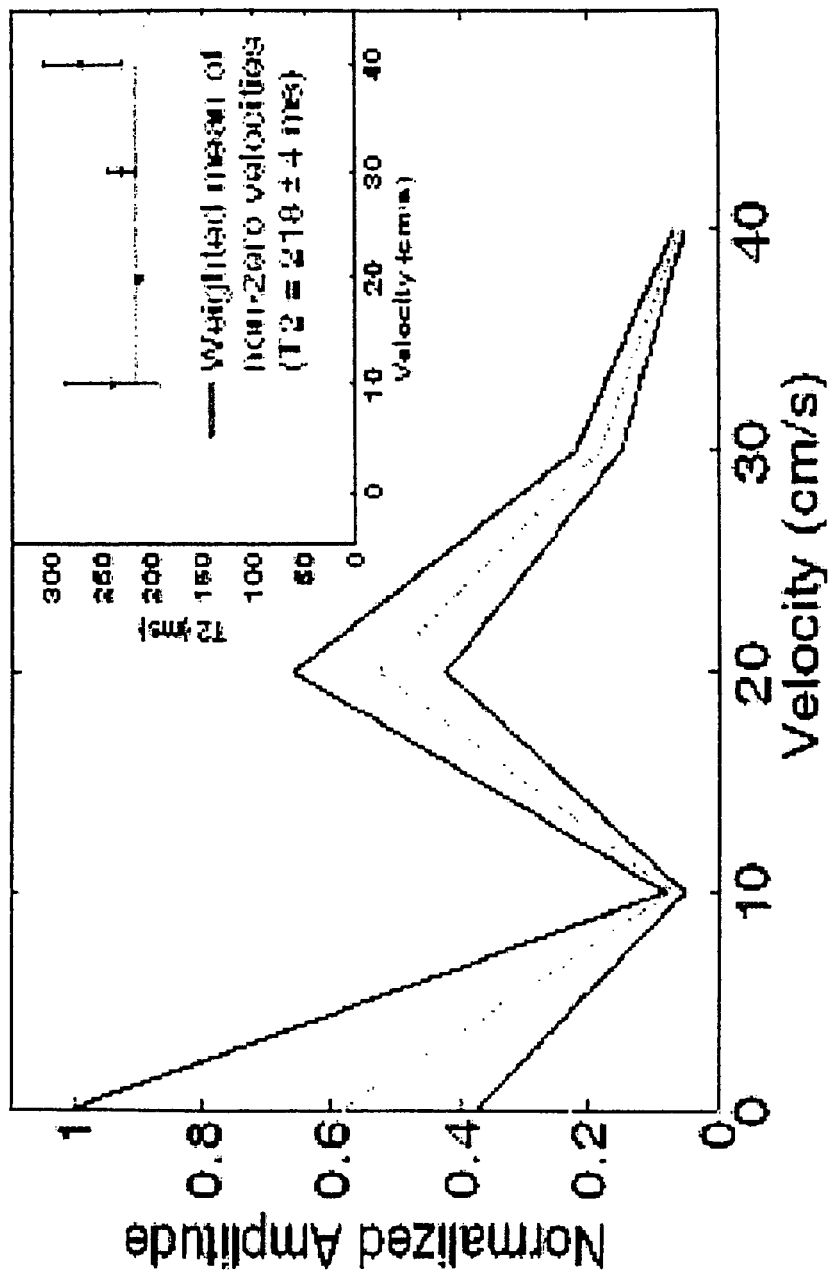
FIG. 4 is a plot showing example velocity distributions at different TEs, using an example of the disclosed method and system.

FIG. 4 illustrates an example of T2-weighted velocity distributions using an example of the disclosed method and (inset) velocity-dependent T2 estimates. Experimental velocity spectra were reconstructed from FVE data acquired at four TEs (TE=7.6, 55.4, 103.2, 198.7 ms). The four plots were normalized by the peak amplitude of the early TE spectrum at zero velocity. T2 decay was evident as a decrease in spectral amplitude with increasing TE. Monoexponential fitting of the amplitude for each velocity bin (in this example, 0, 10, 20, 30, 40 cm/s) resulted in a calculated T2 value vs. velocity (inset). The spectra at zero velocity, corresponding to signals from the stationary water bath, exhibited signal decay with a relatively short T2 of 66±4 ms. The accuracy of T2 estimating at higher velocities may depend on the amplitude of the spectrum (i.e., SNR vs. velocity). The weighted-T2 for non-zero velocities (line in inset) was 218±4 ms, agreeing with the separate reference measurement on the tubing fluid alone.

Thus, FIG. 4 may illustrate that the disclosed method may reduce or eliminate one or more errors of the conventional method by separating the tubing and bath fluid signals using FVE. Although the disclosed method may require greater scan time (e.g., by the additional FVE step), it may do so in an SNR-efficient manner while also providing velocity information. Conversely, increasing the spatial resolution of conventional MR oximetry may reduce partial volume effects at the expense of SNR.

In another example study, an example of the disclosed method and system is used to calculate T2 and oxygen saturation in a phantom. The disclosed method is compared with a conventional method.

The setup for this example study may be similar to that described above (using a phantom including tubing in a water bath), although the T1, T2 and TE times may be different.

Figure 6:
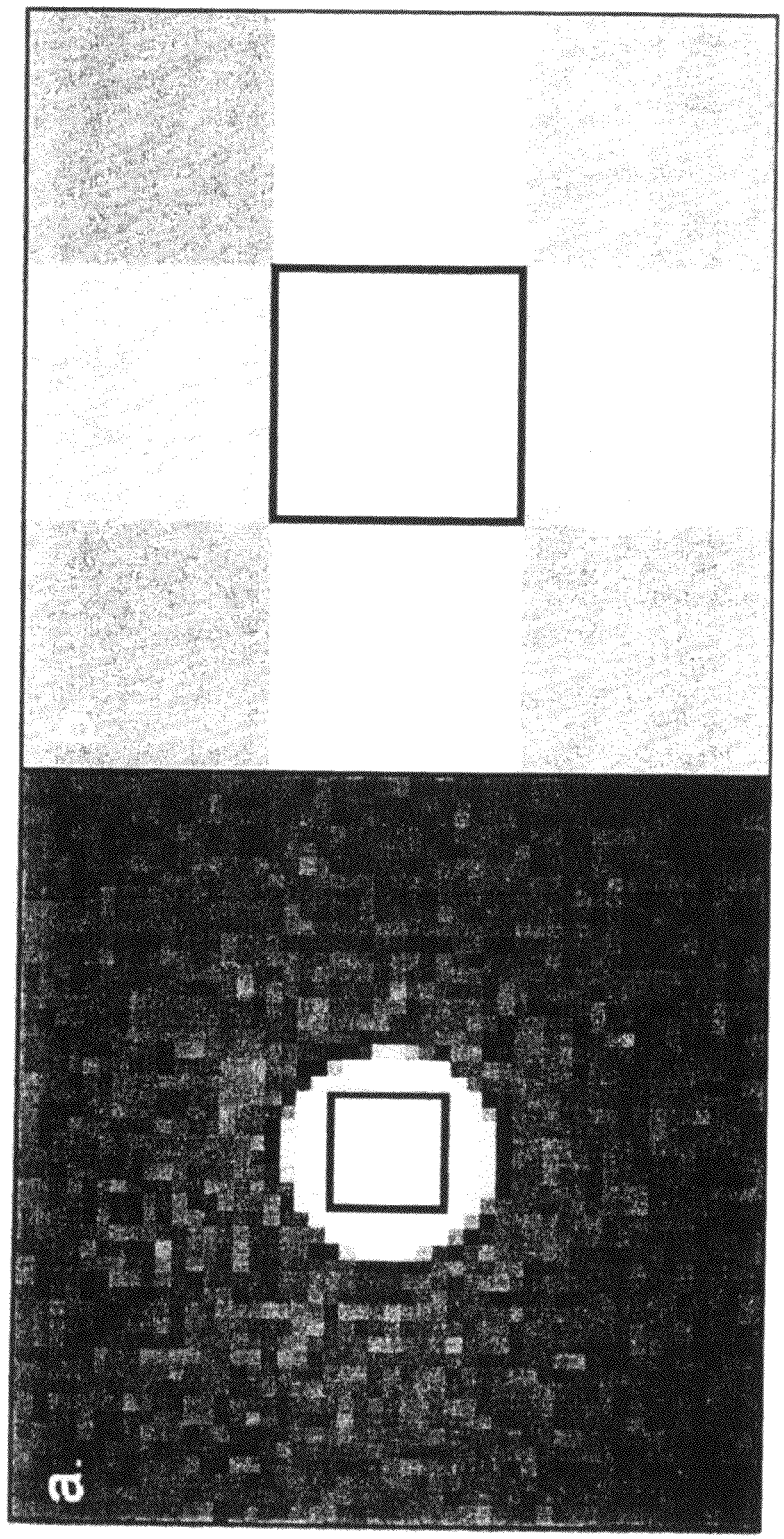
FIG. 6 shows other examples of image slices acquired in a phantom at low and high spatial resolutions.

FIG. 6 shows example images of the phantom acquired at TE=195 ms at a relatively high spatial resolution of 0.8 mm (left image) and at a relatively low spatial resolution of 14.4 mm (right image). The ROIs used for T2 measurements in this example are indicated by a bolded box. The high spatial resolution image was used as a reference and not used for calculations.

Figure 7:
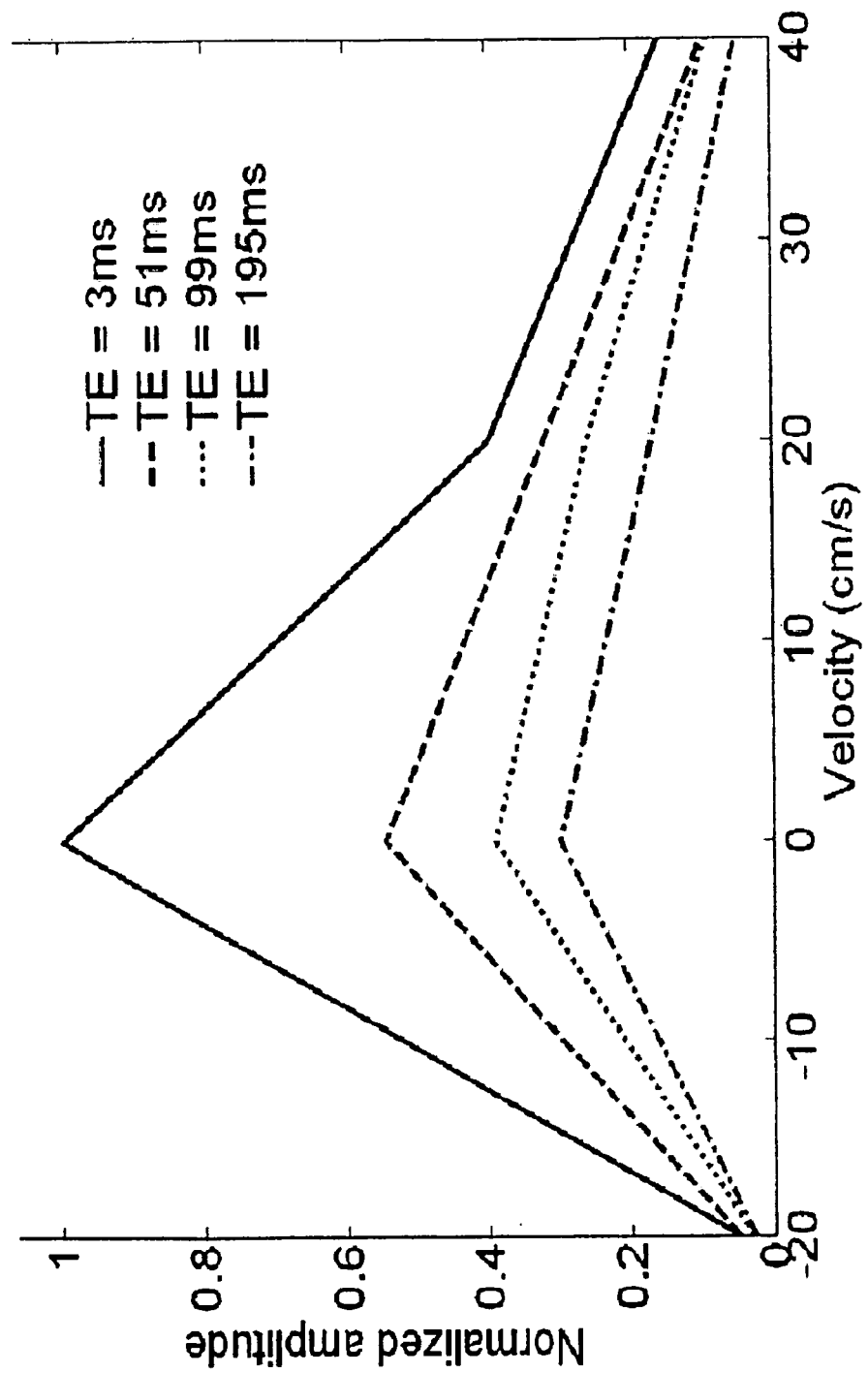
FIG. 7 is a plot showing other example velocity distributions at different TEs, using an example of the disclosed method and system.

FIG. 7 is a chart showing example T2-weighted velocity distributions acquired using an example of the disclosed method. Here, TE times were TE=3, 51, 99, 195 ms.

Figure 8:
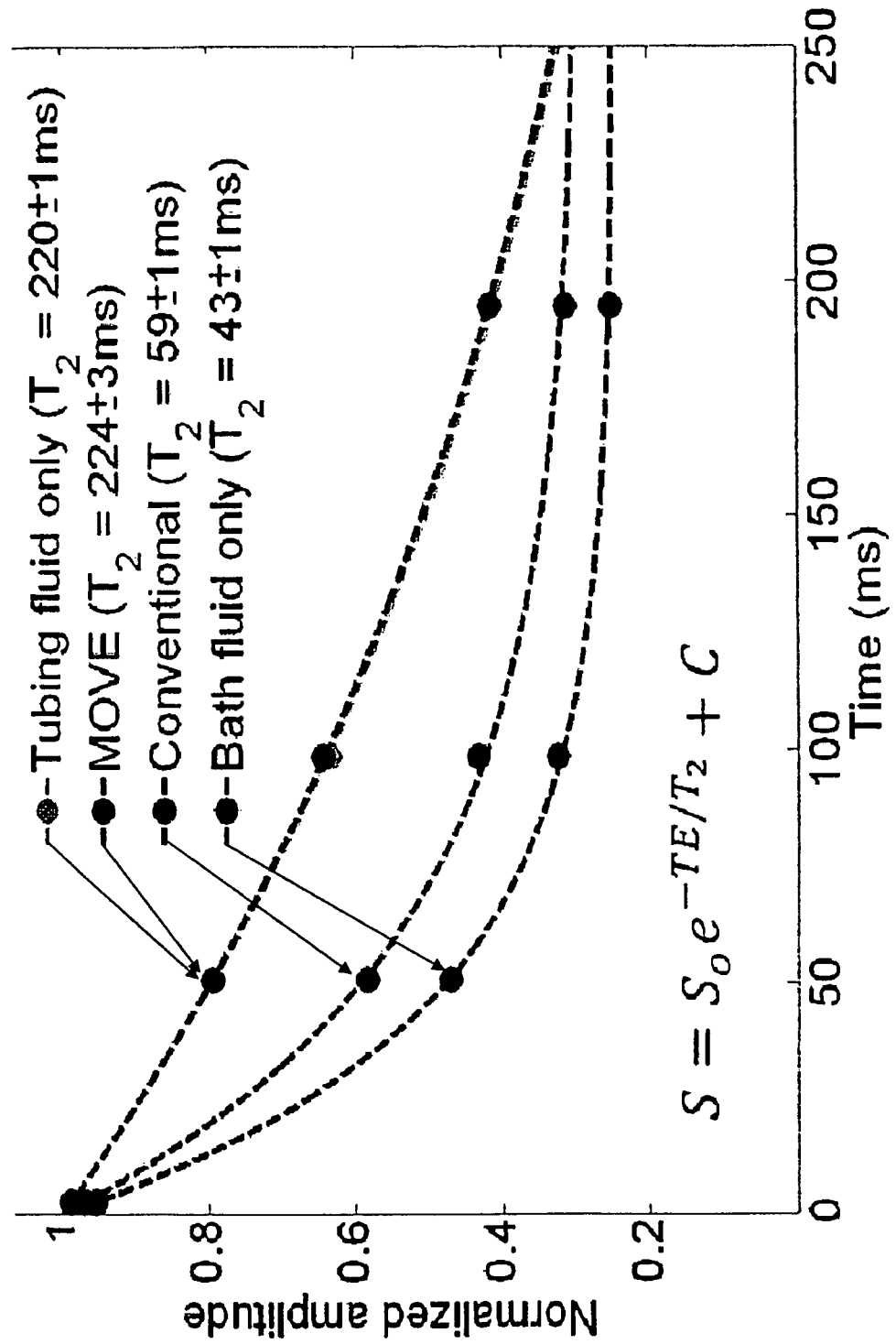
FIG. 8 is a plot showing other example T2 decay curves using an example of the disclosed method and system, compared to an example conventional method.

FIG. 8 is a chart showing example fitted T2 relaxation curves obtained using an example conventional method and an example of the disclosed method (also referred to as "MOVE"), at 14.4 mm spatial resolution, as well as conventional measurements of isolated tubing and bath fluid samples. FIG. 8 also includes the equation used in calculations and the calculated T2 values. The calculations gave T2 values as follows: tubing fluid only, T2=220±1 ms; disclosed method, T2=224±3 ms; conventional method, T2=59±1 ms; bath fluid only, T2=43±1 ms. As indicated in FIG. 8, the T2 estimate obtained using the conventional method indicates significant underestimation, which may be due to partial volume effects. In contrast, the T2 estimate obtained using an example of the disclosed method, based on the 20 cm/s velocity peak (e.g., as shown in FIG. 7) indicates separation of tubing and bath fluid signals in the velocity domain, resulting in a more accurate determination of T2 values in the moving fluid, with little or not partial volume effects.

In another example study, an example of the disclosed method is compared with conventional T2 measurements in the neck vessels of an adult volunteer. In this example, gating to the cardiac cycle was used for both the conventional method and the example disclosed method.

In this example, the conventional method employed 4-channel neurovascular array coils, 4 TEs (TE=3, 51, 99, 195 ms), bandwidth of 125 kHz, field-of-view of 150 mm, slice thickness of 5 mm, 3072 points for spiral readout, 11 interleaved readouts, in-plane spatial resolution of 1.0 mm and cardiac phase gating of 700/1200=0.58. In this example, the acquisition time of the conventional method was about 200 seconds.

In this example, the example of the disclosed method employed a body coil, 4 TEs (TE=3, 51, 99, 195 ms), bandwidth of 125 kHz, field-of-view of 480 mm, slice thickness of 5 mm, 3072 points per interleaf, 3 interleaves, cardiac phase gating of 800/1200=0.67, velocity encoding of 40 cm/s, 4 velocity encodings and through-plane velocity resolution of 20 cm/s. In this example, the acquisition time of the example disclosed method was about 64 seconds.

Figure 9:
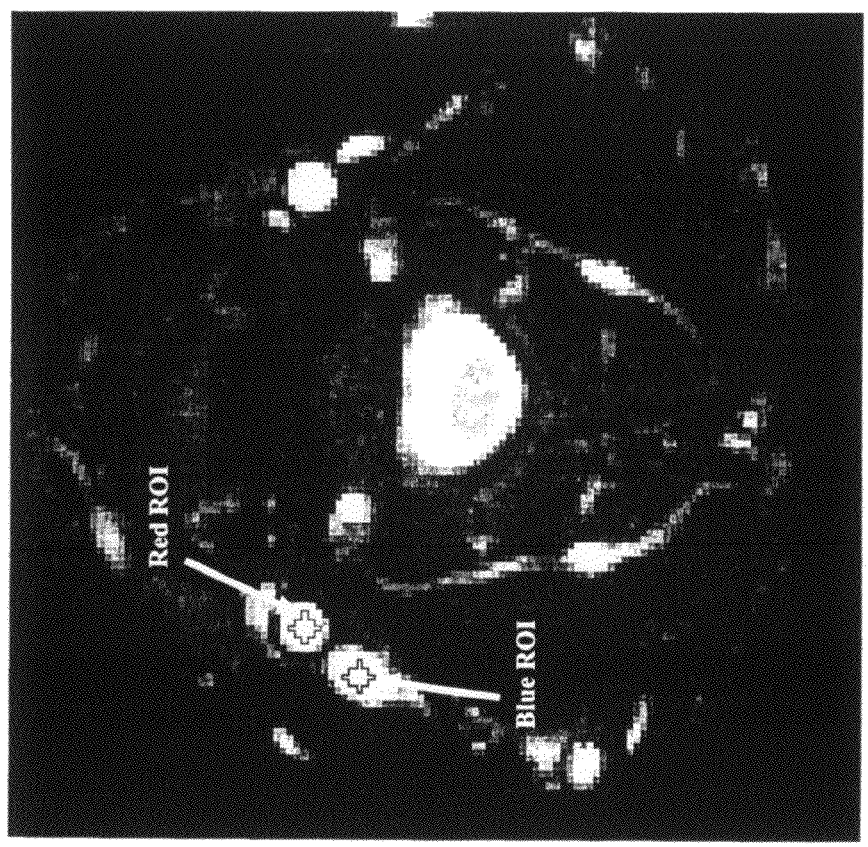
FIG. 9 is an example image generated by conventional T2 measurements in neck vessels of an adult.

FIG. 9 shows an example image obtained from the neck vessels of the adult volunteer using a conventional method and conventional T2 measurement. This may be considered the gold standard against which the disclosed method may be compared. In this example, TE was about 99 ms. Blue and red ROIs have been selected (e.g., by a clinician), designating regions from which internal jugular vein (IJV) and common carotid artery (CCA) data were obtained, respectively.

Figure 10:
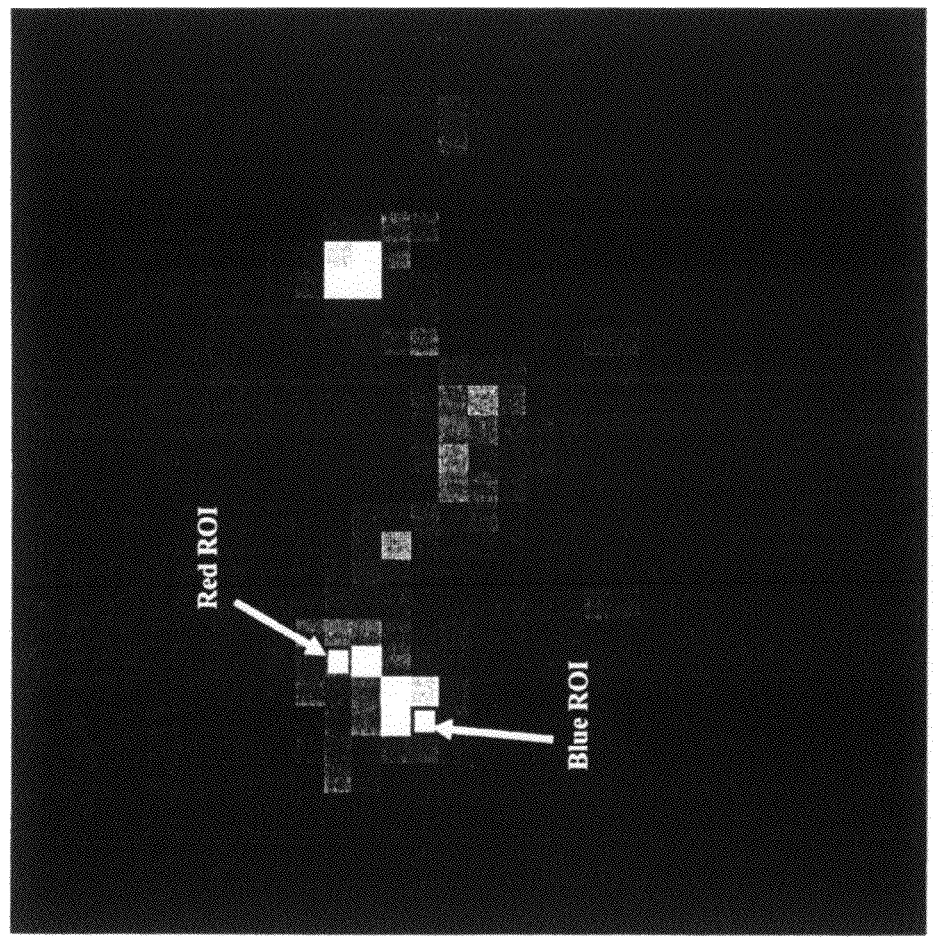
FIG. 10 is an example image generated by an example of the disclosed method in neck vessels of an adult.

FIG. 10 shows an example velocity image obtained using an example of the disclosed method in the same neck vessels of the adult volunteer. Again, blue and red ROIs have been selected (e.g., by a clinician), designating regions from which IJV and CCA data were obtained, respectively.

In the examples of FIGS. 9 and 10, the scanning time using the conventional method was about 200 seconds, while the scanning time using the example of the disclosed method was about 64 seconds.

Figure 11:
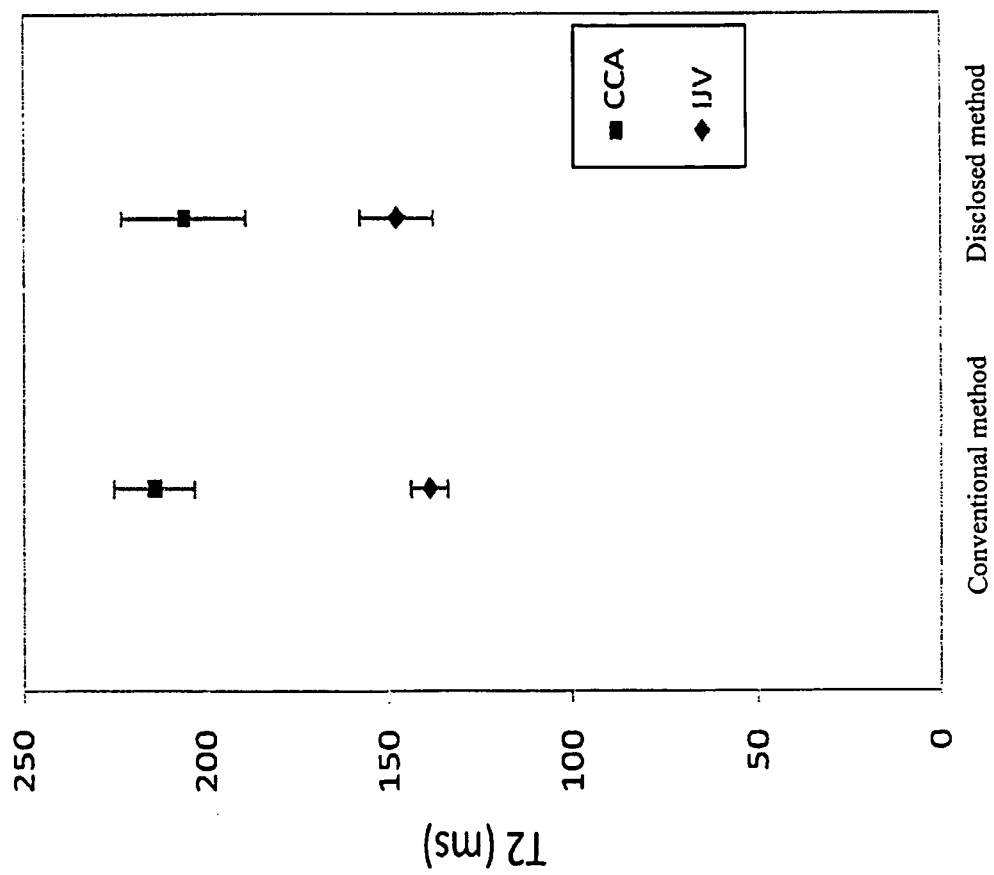
FIG. 11 is a chart comparing calculated T2 values from the images of FIG. 9 and FIG. 10.

FIG. 11 is a chart comparing example calculated T2 values obtained from the conventional method (as illustrated in FIG. 9) with those obtained from an example of the disclosed method (as illustrated in FIG. 10). The calculated T2 values may be considered substantially similar. In this chart, errors may represent uncertainty in the T2 parameter arising from fitting of the exponential decay curves. Both acquisitions using the conventional method and the example disclosed method assumed a 30 cm field-of-view, in order to simulate a fetal scan.

Conventional clinical % $HbO_2$ measurement techniques may include cardiac catheterization and pulse oximetry. The former is invasive, carrying a risk of stroke, haemorrhage, and death and the latter is typically limited to peripheral surface vessels, making both approaches inappropriate for certain applications, such as fetal observation. The disclosed method is noninvasive and may be applied to vessels throughout the cardiovascular system, for example including vessels in fetal patients and in smaller adult vessels. As explained above, the disclosed method may improve upon conventional MR oximetry by overcoming partial volume effects while resulting in shorter scan times. The disclosed method may allow blood oxygen to be studied in the fetal circulation which may be currently difficult or impossible without invasive methods. The disclosed method may also provide information on blood flow.

In general, the disclosed method and system may be used for extracting velocity-based information from MR images. In particular, the disclosed method and system may be useful for differentiating signals from flowing or non-zero velocity tissues from static or zero velocity tissues in a single voxel. The separated non-zero velocity signals may be used for T2 calculations, flow calculations and other such calculations without suffering from partial volume effects.

Other Studies

Other studies that may be carried out to examine the usefulness of the disclosed method may include, for example:
1) Simulation study: Comparison to conventional MR oximetry using a computer model. An example computer model may consist of two concentric circles, in which the inner circle represents a vessel and the outer circle represents surrounding tissue. Both regions may be assigned a T2 value. The model's spatial resolution and SNR may be varied to investigate a range of realistic imaging conditions. For each condition, the conventional method and an example of the disclosed method may be evaluated based on T2 accuracy within the vessel.
2) Phantom study: Programming a conventional MR system with suitable changes to perform FVE and comparing an example of the disclosed method to a conventional method experimentally. The set-up may mimic pulsatile blood flowing in a vessel. Blood-mimicking fluid (e.g., having similar T2 and viscosity) may be pumped though a thin-walled tube passing through the MR scanner. The tube may also be immersed in a water bath doped with a gadolinium contrast agent to mimic static tissue surrounding the vessel. The T2 of the fluid may be measured using both conventional MR oximetry and an example of the disclosed method, and their respective accuracies may compared, such as against predictions from a simulation study.

3) Patient study: Comparison in vessels, such as the aorta and inferior vena cava, of patients (e.g., adults or infants). In adult patients, the relatively wide vessels may allow accurate T2 measurements using conventional MR oximetry, which may provide a gold standard for comparison. A comparison using infant patients may offer a practical example of the usefulness of the disclosed method.

Applications

Although the present disclosure describes the use of the disclosed method and system for determining blood oxygen saturation in flowing blood, other applications may be possible. Such applications may include, for example:

1) Flow calculation—using the velocity distribution, mean flow may be calculated for the non-zero velocities. This may additionally be combined with other measurements. For example, this may be combined with the measured cross-sectional area of the vessel to determine a mean flux.

2) Oxygen flux calculation—using the velocity distribution, mean flow may be calculated for the non-zero velocities. Combined with calculated blood oxygen saturation, this may provide mean oxygen flux.

3) Temporal mean velocity—the temporal mean velocity of blood (e.g., over one or more cardiac cycles) may be determined by acquiring velocity-encoded MR data without gating to the cardiac cycle.

4) Use in other organs—the disclosed method may be used in other organs where there are moving and non-moving tissues, for example the heart, and other arteries and veins. For example, the disclosed method and system may be useful for smaller vessels, such as distal vessels. For some organs (e.g., the heart), myocardial motion may be significant and it may be useful to gate image acquisition to the cardiac cycle (e.g., at diastasis).

The embodiments of the present disclosure described above are intended to be examples only. Alterations, modifications and variations to the disclosure may be made without departing from the intended scope of the present disclosure. Selected features from one or more of the above-described embodiments may be combined to create alternative embodiments not explicitly described. All values and sub-ranges within disclosed ranges are also disclosed. The subject matter described herein intends to cover and embrace all suitable changes in technology. All references mentioned are hereby incorporated by reference in their entirety.

REFERENCES

U.S. Pat. No. 5,233,991
Wright et al. J Magn Reson Imag 1:275-283 (1991)
Stainsby et al. Magn Reson Med 40:494-499 (1998)
Carvalho et al. Magn Reson Med 57:639-646 (2007)

The invention claimed is:

1. A method for measuring oxygen saturation in blood flowing in a vessel using magnetic resonance (MR), the method comprising:
   obtaining by at least one processor non-transitory signals representing an MR image sequence of the vessel from an MR acquisition device, the MR image sequence including a plurality of image data sets with different echo time (TE) encoding, and different Fourier velocity encoding (FVE), the FVE being obtained using different bipolar gradients having different amplitudes to encode respective different velocities for each TE, the FVE defining a velocity dimension in the MR image sequence;
   for each TE, applying by the at least one processor a Fourier transformation along the velocity dimension to measure a velocity distribution of non-transitory tissue signals in each voxel of the MR image sequence;
   measuring by the at least one processor non-transitory tissue signals indicative of flowing blood apart from non-transitory tissue signals indicative of static tissue, based on the velocity distribution; and
   determining measuring by the at least one processor oxygen saturation in blood using only the non-transitory tissue signals indicative of flowing blood;
   outputting by the at least one processor non-transitory signals representative of the measured oxygen saturation to make available to a user or a device.

2. The method of claim 1 further comprising:
   a display device for displaying the non-transitory signals representative of the measured oxygen saturation to the user.

3. The method of claim 1 wherein each bipolar gradient is aligned with the direction of flow, perpendicular to an imaging plane.

4. The method of claim 1 wherein, for acquisition of each image data, the respective bipolar gradient are applied immediately after a spectral-spatial RF pulse and induces a velocity-dependent phase shift in proton spins.

5. The method of claim 1 wherein measuring oxygen saturation in blood comprises measuring T2 decay based on the non-transitory tissue signals indicative of flowing blood only.

6. The method of claim 1 wherein the non-transitory tissue signals indicative of flowing blood is measured based on a velocity distribution having a range of non-zero velocities and the non-transitory tissue signals indicative of static tissue is measured based on a velocity distribution having a peak at zero velocity.

7. The method of claim 1 further comprising measuring, using at least one of the velocity distribution and the oxygen saturation, one of: a mean flow rate, a mean oxygen flux, and a mean velocity over time.

8. The method of claim 1 further comprising applying a plurality of pulse sequences including TE and FVE for acquiring the MR image sequence.

9. A system for measuring oxygen saturation in blood flowing in a vessel using magnetic resonance (MR), the system comprising:
   an MR acquisition device for acquiring non-transitory signals representing an MR image sequence of the vessel, the MR image sequence including a plurality of image data sets with different echo time (TE) encoding, and different Fourier velocity encoding (FVE), the FVE being obtained using different bipolar gradients having different amplitudes to encode respective different velocities for each TE, the FVE defining a velocity dimension in the MR image sequence;
   at least one processor for executing instructions configured to:
      receive the non-transitory signals from the MR acquisition device;
      for each TE, apply a Fourier transformation along the velocity dimension to measure a velocity distribution of non-transitory tissue signals in each voxel of the MR image sequence;

measure non-transitory tissue signals indicative of flowing blood apart from non-transitory tissue signals indicative of static tissue, based on the velocity distribution;

measure oxygen saturation in blood using only the non-transitory tissue signals indicative of flowing blood; and output non-transitory signals representative of the measured oxygen saturation to make available to a user or a device.

10. The system of claim 9 further comprising a display device for displaying to the user at least one of: the velocity distribution, the measured non-transitory tissue signals indicative of flowing blood, and the measured oxygen saturation in blood.

11. The system of claim 10 wherein the MR image acquisition device is configured to apply a plurality of pulse sequences including TE and FVE for acquiring the MR image sequence.

12. The system of claim 10 wherein the MR image acquisition device is configured to align each bipolar gradient with the direction of flow, perpendicular to an imaging plane.

13. The system of claim 10 wherein the MR image acquisition device is configured to apply the bipolar gradient immediately after a spectral-spatial RF pulse, and wherein the bipolar gradient induces a velocity-dependent phase shift in proton spins.

14. The system of claim 9 wherein measuring oxygen saturation in blood comprises measuring T2 decay based on the tissue signals indicative of flowing blood only.

15. The system of claim 9 wherein the tissue signals indicative of flowing blood is measured based on a velocity distribution having a range of non-zero velocities and the non-transitory tissue signals indicative of static tissue is measured based on a velocity distribution having a peak at zero velocity.

16. The system of claim 9 wherein the at least one processor is configured to further execute instructions to cause the system to measure, using at least one of the velocity distribution and the oxygen saturation, one of: a mean flow rate, a mean oxygen flux, and a mean velocity over time.

17. A non-transient computer readable medium for storing program instructions that, when executed by at least one processor causes the at least one processor to perform a method for measuring oxygen saturation in blood flowing in a vessel using magnetic resonance (MR), comprising:

obtaining non-transitory signals representing an MR image sequence of the vessel from an MR acquisition device, the MR image sequence including a plurality of image data sets with different echo time (TE) encoding, and different Fourier velocity encoding (FVE), the FVE being obtained using different bipolar gradients having different amplitudes to encode respective different velocities for each TE, the FVE defining a velocity dimension in the MR image sequence;

for each TE, applying a Fourier transformation along the velocity dimension to measure a velocity distribution of non-transitory tissue signals in each voxel of the MR image sequence;

measuring non-transitory tissue signals indicative of flowing blood apart from non-transitory tissue signals indicative of static tissue, based on the velocity distribution;

measuring oxygen saturation in blood using only the non-transitory tissue signals indicative of flowing blood; and making available non-transitory signals representative of the measured oxygen saturation.

18. The non-transient computer readable medium of claim 16 further comprising program instructions that, when executed by at least one processor, causes the at least one processor to perform the method further comprising:

outputting the non-transitory signals representative of the measured oxygen saturation for display on a display device.

19. The non-transient computer readable medium of claim 16 wherein each bipolar gradient is aligned with the direction of flow, perpendicular to an imaging plane.

20. The non-transient computer readable medium of claim 16 wherein, for acquisition of each image data, the respective bipolar gradient are applied immediately after a spectral-spatial RF pulse and induces a velocity-dependent phase shift in proton spins.

21. The non-transient computer readable medium of claim 16 wherein measuring oxygen saturation in blood comprises measuring T2 decay based on the tissue signals indicative of flowing blood only.

22. The non-transient computer readable medium of claim 16 wherein the non-transitory tissue signals indicative of flowing blood is measured based on a velocity distribution having a range of non-zero velocities and the non-transitory tissue signals indicative of static tissue is measured based on a velocity distribution having a peak at zero velocity.

23. The non-transient computer readable medium of claim 16 further comprising program instructions that, when executed by at least one processor, causes the at least one processor to perform the method further comprising measuring, using at least one of the velocity distribution and the oxygen saturation, one of: a mean flow rate, a mean oxygen flux, and a mean velocity over time.

24. The non-transient computer readable medium of claim 16 further comprising program instructions that, when executed by at least one processor, causes the at least one processor to perform the method further comprising applying a plurality of pulse sequences including TE and FVE for acquiring the MR image sequence.

* * * * *